US006964953B2

(12) United States Patent
Belanoff

(10) Patent No.: US 6,964,953 B2
(45) Date of Patent: Nov. 15, 2005

(54) METHODS FOR TREATING STRESS DISORDERS USING GLUCOCORTICOID RECEPTOR-SPECIFIC ANTAGONISTS

(75) Inventor: Joseph K. Belanoff, Woodside, CA (US)

(73) Assignee: Corcept Therapeutics, Inc., Menlo Park, CA (US)

( * ) Notice: Subject to any disclaimer, the term of this patent is extended or adjusted under 35 U.S.C. 154(b) by 0 days.

(21) Appl. No.: 10/102,448

(22) Filed: Mar. 19, 2002

(65) Prior Publication Data

US 2002/0169152 A1    Nov. 14, 2002

Related U.S. Application Data

(60) Provisional application No. 60/278,523, filed on Mar. 23, 2001.

(51) Int. Cl.[7] .............................................. A61K 31/56
(52) U.S. Cl. ...................... 514/178; 514/179
(58) Field of Search ................................ 514/178, 179

(56) References Cited

U.S. PATENT DOCUMENTS 5,447,951 A  *  9/1995  Politi et al. .................. 514/419
6,150,349 A  * 11/2000  Schatzberg et al. ......... 514/179
6,441,015 B2*  8/2002  Aspnes et al. ............... 514/381

FOREIGN PATENT DOCUMENTS

| EP | 1 157 695 A1 | 11/2001 |
| WO | WO 99/17779 A1 | 4/1999 |
| WO | WO 00/54766 A1 | 9/2000 |
| WO | WO 01/37840 | 5/2001 |

OTHER PUBLICATIONS

Behl, C. et al., (1997), "Protection against oxidative stress-induced neuronal cell death-A novel role for RU486," *European J. of Neurosci.*, 9:912-920.
Heim, C. et al., (1999), "The potential role of hypocortisolism in the pathophysiology of stress-related bodily disorders," *Psychoneuroendocrinology*, 25:1-25.
Sapolsky, R. et al., (1994), "The physiological relevance of glucocorticoid endangement of the hippocampus," *Ann NY Acad. Sci.* 746:294-304.
Starkman, M. et al., (1999), "Decrease in cortisol reverses human hippocampal atrophy following treatment of Cushing's disease," *Biol Psychiatry*, 46: 1595-1602.
Yedua, R., (2000), "Biology of posttraumatic stress disorder, " *J Clin. Psychiarty*, 61 Suppl 7(5):14-21.
Porter, N. et al., (1998), "Stress Hormone and Brain Aging: Adding Insult to Injury?," *Nature Neuroscience*, 1:1, pp. 3-4.
Sapolsky, R., (2000), "Glucocorticoids and Hippocampal Atrophy in Neuropsychiatric Disorders," *Arch Gen Psychiatry*, 57:925-935.
Cherkin et al., "Interruption by Halothane of Memory Consolidation in Chicks", *Fed. Proc.*, 24: 328 (1995).
Shors, "Acute Stress Rapidly and Persistently Enhances Memory Formation in the Male Rat", *Neurobiol. Learn. Mem.* 75: 10-29 (2001).
Sandi et al., "Corticosteroid Receptor Antagonists are Amnestic for Passive Avoidance Learning in Day-old Chicks", *Euro. J. Neurosci* . 6: 1292-1297 (1994).
Sandi et al., "Experience-dependent Facilitating Effect of Corticosterone on Spatial Memory Formation in the Water Maze", *Euro. J. Neurosci.* 9: 637-642 (1997).
Van Der Lely, A.J., et al., "Rapid Reversal of Acute Psychosis in the Cushing Syndrome with the Cortisol-Receptor Antagonist Mitepristone (RU 486)," *Annals of Internel Medicine*, Jan. 15, 1991, pp. 143-144, vol. 114, No. 2, New York, NY.

* cited by examiner

*Primary Examiner*—Barbara P. Badio
(74) *Attorney, Agent, or Firm*—Townsend and Townsend and Crew LLP

(57) ABSTRACT

This invention generally pertains to the field of psychiatry. In particular, this invention pertains to the discovery that agents which inhibit the binding of cortisol to its receptors can be used in methods for treating stress disorders. Mifepristone, a potent specific glucocorticoid receptor antagonist, can be used in these methods. The invention also provides a kit for treating stress disorders in a human including a glucocorticoid receptor antagonist and instructional material teaching the indications, dosage and schedule of administration of the glucocorticoid receptor antagonist.

16 Claims, No Drawings

US 6,964,953 B2

METHODS FOR TREATING STRESS DISORDERS USING GLUCOCORTICOID RECEPTOR-SPECIFIC ANTAGONISTS

CROSS REFERENCE TO RELATED APPLICATIONS

This application claims priority to U.S. patent application Ser. No. 60/278,523 filed Mar. 23, 2001, which is explicitly incorporated herein by reference in its entirety and for all purposes.

FIELD OF THE INVENTION

This invention generally pertains to the field of psychiatry. In particular, this invention pertains to the discovery that agents which inhibit the binding of cortisol to the glucocorticoid receptor can be used in methods of treating stress related disorders.

INTRODUCTION

Stress disorders are environmentally induced psychiatric conditions. Exposure to one or more traumatic stressful events can lead to acute or extended periods in which the victim experiences dissociative symptoms and re-experiences the traumatic event. In some individuals, exposure to traumatic stressors can even induce brief episodes of mental dysfunction and disorganization so severe as to be classified as psychotic. While antidepressant drugs such as selective serotonin reuptake inhibitors, tricyclics, and monoamine oxidase inhibitors have shown promise in trials against Post-Traumatic Stress Disorder, there is no currently available pharmacotherapy generally effective against stress disorders in general or in mixed patient populations. See Marshall & Pierce, *Harvard Rev Psychiatry* 7:247–55 (2000).

Cortisol, which is secreted in response to ACTH (corticotropin), shows circadian rhythm variation, and further, is an important element in responsiveness to many physical and psychological stresses. It has been proposed that, with age, the cortisol regulatory system becomes hyperactivated in some individuals, resulting in hypercortisolemia. It has additionally been postulated that high levels of cortisol are neurotoxic, particularly in the hippocampus, a brain structure that is thought to be central to the processing and temporary storage of complex information and memory (see, e.g., Sapolsky et al., *Ann. NY Acad. Sci.* 746:294–304, 1994; Silva, *Annu. Rev. Genet.* 31:527–546, 1997; de Leon et al., *J. Clin. Endocrinol & Metab.* 82:3251, 1997; Maeda et al., supra).

Persistent high levels of circulating cortisol are associated with loss of volume in the hippocampus. See Starkman et al., *Biol Psychiatry* 32:756–764, 1992. Moreover, surgical treatment of the adrenal glands to reduce excessive cortisol secretion can reverse the hippocampal atrophy caused by high cortisol levels. See Starkman et al., *Biol Psychiatry* 46:1595–602, 1999. Hippocampal atrophy is also a characteristic of Post-Traumatic stress disorder, and there is evidence to suggest that elevated levels of glucocorticoids associated with stress disorders contribute to loss of hippocampal volume. See Sapolsky, *Arch Gen Psychiatry* 57:925–935 (2000).

Despite the association between stress and cortisol secretion, evidence has accumulated that many patients suffering from persistent stress disorders have lowered, rather than elevated, cortisol levels. See Heim et al., *Psychoneuroendocrinology* 25:1–25 (2000). Hypocortisolism in stress disorder patients may be reconciled with the elevated cortisol levels brought about by acute stress by assuming that persistent stress disorders represent a persistent state of cortisol hypersensitivity. That is, exposure to acute stressors may trigger negative feedback mechanisms that ultimately lead to decreased cortisol secretion. Persistently low levels of cortisol may leave the hypothalamic-pituitary-adrenal axis 'primed' to respond to even minor elevations in circulating glucocorticoid levels. As a result, minor stressors—resulting in small elevations in glucocorticoid levels—can provoke traumatic responses in patients suffering from persistent stress disorders. See Yehuda, *J Clin Psychiatry* 61 Suppl 7(5):14–21 (2000).

There has been no evidence prior to this invention, however, that a glucocorticoid receptor antagonist can be an effective treatment for stress disorders, especially in patients having cortisol levels that fall within a normal range. Many of the actions of cortisol are mediated by binding to the type I (mineralocorticoid) receptor, which is preferentially occupied, relative to the type II (glucocorticoid) receptor, at physiological cortisol levels. As cortisol levels increase, more glucocorticoid receptors are occupied and activated. Because cortisol plays an essential role in metabolism, inhibition of all cortisol-mediated activities, however, would be fatal. Therefore, antagonists that specifically prevent glucocorticoid receptor functions, but do not antagonize mineralocorticoid receptor functions are of particular use in this invention. Mifepristone and similar antagonists are examples of this category of receptor antagonists.

Mifepristone has been noted as being effective at abrogating some of the age-associated electrophysiological changes in the rat hippocampus (Talmi et al., *Neurobiol. of Aging* 17:9–14, 1996) and also as providing protection against oxidative stress-induced neuronal cell death in the mouse hippocampus (Behl et al., *European J. of Neuorsci.* 9:912–920, 1997). There have been no studies, however, that have shown that mifepristone can forestall or reverse the loss of hippocampal atrophy associated with stress disorders.

The present inventor has determined that glucocorticoid receptor antagonists such as mifepristone are effective agents for the specific treatment of stress disorders in patients with normal or decreased cortisol levels. The present invention therefore fulfills the need for an effective treatment for stress disorders by providing methods of administering glucocorticoid receptor antagonists to treat patients diagnosed with stress disorders.

SUMMARY OF THE INVENTION

The invention provides a method of ameliorating the symptoms of a stress disorder in a patient who has normal or decreased cortisol levels. The method comprises administration of a therapeutically effective amount of a glucocorticoid receptor antagonist to the patient, who may be diagnosed with Post-Traumatic Stress Disorder, Acute Stress Disorder, or Brief Psychotic Disorder with Marked Stressor (s).

In one embodiment of the invention, the method of treating a stress disorder uses a glucocorticoid receptor antagonist comprising a steroidal skeleton with at least one phenyl-containing moiety in the 11-beta position of the steroidal skeleton. The phenyl-containing moiety in the 11-beta position of the steroidal skeleton can be a dimethylaminophenyl moiety. In alternative embodiments, the glucocorticoid receptor antagonist comprises mifepristone, or, the glucocorticoid receptor antagonist is selected from the group consisting of RU009 and RU044.

In other embodiments, the glucocorticoid receptor antagonist is administered in a daily amount of between about 0.5 to about 20 mg per kilogram of body weight per day; between about 1 to about 10 mg per kilogram of body weight per day; or between about 1 to about 4 mg per kilogram of body weight per day. The administration can be once per day. In alternative embodiments, the mode of glucocorticoid receptor antagonist administration is oral, or by a transdermal application, by a nebulized suspension, or by an aerosol spray.

The invention also provides a method of preventing, delaying, or lessening the emergence of stress disorder symptoms in a patient who has been exposed to a traumatic stressor, but who has not yet developed the characteristic symptoms of a stress disorder. The method comprises administering an effective amount of a glucocorticoid receptor antagonist to the patient within 30 days of exposure to a traumatic stressor.

The invention also provides a kit for the treatment of a stress disorder in a human, the kit comprising a glucocorticoid receptor antagonist; and, an instructional material teaching the indications, dosage and schedule of administration of the glucocorticoid receptor antagonist. In alternative embodiments, the instructional material indicates that the glucocorticoid receptor antagonist can be administered in a daily amount of about 0.5 to about 20 mg per kilogram of body weight per day, of about 1 to about 10 mg per kilogram of body weight per day, or about 1 to about 4 mg per kilogram of body weight per day. The instructional material can indicate that cortisol contributes to the stress-induced symptoms in patients with stress disorders, and that the glucocorticoid receptor antagonist can be used to treat stress disorders. In one embodiment, the glucocorticoid receptor antagonist in the kit is mifepristone. The mifepristone can in tablet form.

A further understanding of the nature and advantages of the present invention is realized by reference to the remaining portions of the specification and claims.

All publications, patents and patent applications cited herein are hereby expressly incorporated by reference for all purposes.

DEFINITIONS

The term "treating" refers to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, the methods of the invention success fully treat a patient's stress disorders by decreasing the incidence of dissociative symptoms, re-experience of traumatic events, or psychotic behavior.

The term "stress disorder" refers to a psychiatric condition precipitated by exposure to a traumatic or stressful event. Stress disorders include Acute Stress Disorder, Post-Traumatic Stress Disorder, and Brief Psychotic Disorder with Marked Stressor(s).

The term "Acute Stress Disorder" refers to a psychiatric condition in its broadest sense, as defined in American Psychiatric Association: Diagnostic and Statistical Manual of Mental Disorders, Fourth Edition, Text Revision, Washington, D.C., 2000 ("DSM-IV-TR"). The DSM-IV-TR defines "Acute Stress Disorder" as characterized by anxiety, dissociative, and other symptoms occurring within 1 month after exposure to an extreme traumatic stressor. The DSM-IV-TR sets forth a generally accepted standard for diagnosing and categorizing Acute Stress Disorder.

The term "Post-Traumatic Stress Disorder" refers to a psychiatric condition in its broadest sense, as defined in DSM-IV-TR. The DSM-IV-TR defines "Post-Traumatic Stress Disorder" as characterized by persistent re-experiencing of an extreme traumatic event. The DSM-IV-TR sets forth a generally accepted standard for diagnosing and categorizing Post-Traumatic Stress Disorder.

The term "Brief Psychotic Disorder with Marked Stressor(s)" refers to a psychiatric condition in its broadest sense, as defined in DSM-IV-TR. The DSM-IV-TR defines "Brief Psychotic Disorder with Marked Stressor(s)" as a sudden but brief onset of psychotic symptoms developing shortly after and apparently in response to one or more stressful events. The DSM-IV-TR sets forth a generally accepted standard for diagnosing and categorizing Brief Psychotic Disorder with Marked Stressor(s).

The term "cortisol" refers to a family of compositions also referred to hydrocortisone, and any synthetic or natural analogues thereof.

The term "glucocorticoid receptor" ("GR") refers to a family of intracellular receptors also referred to as the cortisol receptor, which specifically bind to cortisol and/or cortisol analogs. The term includes isoforms of GR, recombinant GR and mutated GR.

The term "mifepristone" refers to a family of compositions also referred to as RU486, or RU38.486, or 17-beta-hydroxy-11-beta-(4-dimethyl-aminophenyl)-17-alpha-(1-propynyl)-estra-4,9-dien-3-one), or 11-beta-(4dimethylaminophenyl)-17-beta-hydroxy-17-alpha-(1-propynyl)-estra-4,9-dien-3-one), or analogs thereof, which bind to the GR, typically with high affinity, and inhibit the biological effects initiated/mediated by the binding of any cortisol or cortisol analogue to a GR receptor. Chemical names for RU-486 vary; for example, RU486 has also been termed: 11B-[p-(Dimethylamino)phenyl] -17B-hydroxy-17-(1-propynyl)-estra-4,9-dien-3-one; 11B-(4-dimethyl-aminophenyl)-17B-hydroxy-17A-(prop-1-ynyl)-estra-4,9-dien-3-one; 17B-hydroxy-11B-(4-dimethylaminophenyl-1)-17A-(propynyl-1l)-estra-4,9-diene-3-one; 17B-hydroxy-11B-(4-dimethylaminophenyl-1)-17A-(propynyl-1)-E;(11B,17B)-11-[4-dimethylamino)-phenyl]-17-hydroxy-17-(1-propynyl)estra-4,9-dien-3-one; and 11B-[4-(N,N-dimethylamino)phenyl] -17A-(prop-1-ynyl)-D-4,9-estradiene-17B-ol-3-one.

The term "specific glucocorticoid receptor antagonist" refers to any composition or compound which partially or completely inhibits (antagonizes) the binding of a glucocorticoid receptor (GR) agonist, such as cortisol, or cortisol analogs, synthetic or natural, to a GR. A "specific glucocorticoid receptor antagonist" also refers to any composition or compound which inhibits any biological response associated with the binding of a GR to an agonist. By "specific", we intend the drug to preferentially bind to the GR rather than the mineralocorticoid receptor (MR) at a rate of at least 100-fold, and frequently 1000-fold.

A patient "not otherwise in need of treatment with a glucocorticoid receptor antagonist" is a patient who is not suffering from a condition which is known in the art to be effectively treatable with glucocorticoid receptor antagonists. Conditions known or reported in the art to be effectively treatable with glucocorticoid receptor antagonists include Cushing's disease, schizophrenia and mania, dementia, delirium, and psychotic major depression.

DETAILED DESCRIPTION OF THE INVENTION

This invention pertains to the surprising discovery that agents that can inhibit glucocorticoid receptor-mediated biological responses are effective for treating stress disorders. In treating stress disorders, the methods of the invention can preferably relieve the symptoms of a stress disorder or lead to complete resolution of the underlying disorder itself In one embodiment, the methods of the invention use agents that act as glucocorticoid receptor (GR) antagonists, blocking the interaction of cortisol with GR, to treat or ameliorate a stress disorder or symptoms associated with a stress disorder. The methods of the invention are effective in ameliorating the symptoms of a stress disorder patient afflicted with either decreased, normal or increased levels of cortisol or other glucocorticoids, natural or synthetic.

Cortisol acts by binding to an intracellular, glucocorticoid receptor (GR). In man, glucocorticoid receptors are present in two forms: a ligand-binding GR-alpha of 777 amino acids; and, a GR-beta isoform that differs in only the last fifteen amino acids. The two types of GR have high affinity for their specific ligands, and are considered to function through the same transduction pathways.

The biologic effects of cortisol, including pathologies or dysfunctions caused by hypercortisolemia, can be modulated and controlled at the GR level using receptor antagonists. Several different classes of agents are able to act as GR antagonists, i.e., to block the physiologic effects of GR-agonist binding (the natural agonist is cortisol). These antagonists include compositions which, by binding to GR, block the ability of an agonist to effectively bind to and/or activate the GR. One family of known GR antagonists, mifepristone and related compounds, are effective and potent anti-glucocorticoid agents in humans (Bertagna, *J. Clin. Endocrinol. Metab.* 59:25, 1984). Mifepristone binds to the GR with high affinity, with a K of dissociation <$10^{-9}$ M (Cadepond, *Annu. Rev. Med.* 48:129, 1997). Thus, in one embodiment of the invention, mifepristone and related compounds are used to treat stress disorders.

Stress disorders typically manifest themselves with a variety of symptoms, including purely psychological symptoms such as re-experiencing traumatic events, physiological reactions such as persistent arousal, and psychiatric symptoms such as psychotic delusions. Thus, a variety of means of diagnosing stress disorders and assessing the success of treatment, i.e., the success and extent the symptoms of stress disorders are lessened by the methods of the invention, can be used, and a few exemplary means are set forth herein. These means can include classical, subjective psychological evaluations and neuropsychiatric examinations as described below.

As the methods of the invention include use of any means to inhibit the biological effects of an agonist-bound GR, illustrative compounds and compositions which can be used to treat stress disorders are also set forth. Routine procedures that can be used to identify further compounds and compositions able to block the biological response caused by a GR-agonist interaction for use in practicing the methods of the invention are also described. As the invention provides for administering these compounds and compositions as pharmaceuticals, routine means to determine GR antagonist drug regimens and formulations to practice the methods of the invention are set forth below.

1. Diagnosis of Acute Stress Disorder

Acute Stress Disorder (ASD) is characterized by a constellation of symptoms, lasting at least two days, that appear and resolve within one month of exposure to an extreme traumatic stressor. If symptoms appear or persist beyond one month after exposure to the traumatic stressor, the patient may be considered to suffer from Post-Traumatic Stress Disorder rather than ASD. ASD is a common precursor to Post-Traumatic Stress Disorder, and up to 80% of trauma survivors initially suffering from ASD will meet the diagnostic criteria for Post-Traumatic Stress Disorder six months later (see Brewin et al., *Am J Psychiatry* 156:360–6, 1999).

Patients develop ASD following exposure to an extreme traumatic stressor (DSM-IV-TR Criterion A). A person must respond to the stressor with intense fear, helplessness, or horror to be diagnosed with ASD. ASD may develop from direct experience of traumatic events, including violent crimes, physical trauma, combat, diagnosis with a life-threatening illness, and natural or manmade disasters. Patients may also develop ASD from witnessing or learning about traumatic events that happen to others, especially family members or close friends. Unexpected exposure to death, dead bodies, or body parts may also induce ASD.

A diagnosis of ASD requires that the person meet several other symptomatic criteria. The person must experience three or more dissociative symptoms in connection with the traumatic stressor (Criterion B). Dissociative symptoms include a subjective sense of numbing or detachment, a reduction in awareness of surroundings, derealization, depersonalization, and dissociative amnesia. Furthermore, ASD requires that the victim persistently re-experience the traumatic event, though recurrent images, thoughts, dreams, illusions, flashbacks, sense of reliving the event, or distress upon exposure to reminders of the event (Criterion C). The person must display marked avoidance of stimuli that arouse recollection of the trauma (Criterion D) and marked symptoms of anxiety or increased arousal (Criterion E). Finally, in addition to the time requirements described above, a diagnosis of ASD requires that the disturbance cause significant distress; or life impairment, and not be due to another psychiatric or physiological condition (Criteria F-H).

ASD may be diagnosed and evaluated with any one of several objective, standardized test instruments known in the art, although skilled clinicians may readily diagnose ASD through unstructured clinical interactions. Standardized test instruments are constructed by experienced clinical researchers based on DSM diagnostic criteria, and are typically validated through statistical studies and comparisons of various patient populations. Generally, standardized instruments assess both manifest psychological or physiological symptoms as well as internal thought processes. Standardized test instruments may comprise structured clinical interviews that are administered by a health care practitioner, or they may comprise self-reporting questionnaires that are completed by the putative patient. Either clinician-administered or self-reported test instruments may be used to identify ASD patients who will benefit from anti-glucocorticoid therapy.

Guidance, procedures and recommendations for test instruments used to diagnose stress disorders may be found in *Standards of Traumatology Practice,* April 2000 revision (Academy of Traumatology, Tallahassee, Fla.). Clinician-administered test instruments for suitable for identifying patients in need of anti-glucocorticoid therapy for ASD include the Acute Stress Disorder Interview (ASDI; Bryant et al., *Psychological Assessment* 10:215–20 (1998)). Self-reported instruments include the modified Stanford Acute Stress Reaction Questionnaire (SASRQ; Cardena et al., *J Traumatic Stress* 13:719–734 (2000)) and the Acute Stress Disorder Scale (ASDS; Bryant et al., *Psychological Assessment* 12:61–68 (2000)). Cutoff scores yielding the most statistically valid division of patients into ASD and non-ASD populations have been established and reported for each test (e.g., a score of 9 or greater for the dissociative cluster and 28 or greater on the reexperiencing, avoidance, and arousal clusters for the ASDS) and may be used to select patients for anti-glucocorticoid therapy.

2. Diagnosis of Post-Traumatic Stress Disorder

Like Acute Stress Disorder, Post-Traumatic Stress Disorder (PTSD) emerges following exposure to an extreme traumatic stressor, and is characterized by persistent reexperiencing of the traumatic event, avoidance of stimuli associated with the trauma, and anxiety or increased arousal. The types of traumatic stressors giving rise to PTSD, and the manifestations of PTSD symptoms, are identical to those described above for ASD, but for three differences. First, the dissociative symptoms required for a diagnosis of ASD are not required for a diagnosis of PTSD, although dissociative symptoms may commonly be seen in PTSD patients. Secondly, PTSD need not arise within one month of exposure to the traumatic stressor, and may emerge months or years after the traumatic event. Thirdly, in contrast to the one month maximum duration of symptoms required for a diagnosis of ASD, symptoms must persist for at least one month in order for a diagnosis of PTSD to be made.

Skilled clinicians routinely diagnose patients with PTSD based on unstructured clinical interactions. Nonetheless, several self-reported and clinician-administered rating scales may be used to diagnose PTSD and are suitable to select patients in need of anti-glucocorticoid therapy. Clinician-administered rating scales include the Structured Interview for PTSD (SI-PTSD; Davidson et al., *J Nervous Mental Disease* 177:336–41 (1989)), the Clinician Administered PTSD Scale (CAPS; Blake et al., *Behavior Therapist* 13:187–8 (1990)) and the Short Screening Scale for DSM-IV PTSD (Breslau et al., *Am J Psychiatry* 156:908–11 (1999)). Suitable self-reported rating scales include the complete and short-form Mississippi Scale for Combat-Related PTSD (Keane et al., *J Consult Clin Psychol* 56:85–90 (1988); Fontana & Rosenbeck, *J Traumatic Stress* 7:407–14 (1994)), the Revised Civilian Mississippi Scale for PTSD (Norris & Perilla, *J Traumatic Stress* 9:285–98 (1996)), and the Davidson Trauma Scale (Davidson et al., *Psychological Med* 27:153–60 (1997)). Similar to the rating scales for ASD, cutoff scores for PTSD diagnosis are determined by selecting a score that yields optimum sensitivity, specificity, positive predictive value and negative predictive value (e.g., a score of 4 or greater on the Short Screening Scale for DSM-IV PTSD; Breslau et al., supra).

3. Diagnosis of Brief Psychotic Disorder with Marked Stressor(s)

A Brief Psychotic Disorder is a short-term (between one day and one month) disturbance involving the sudden onset of at least one psychotic symptom, such as delusions, hallucinations, disorganized speech, or grossly disorganized or catatonic behavior. Brief Psychotic Disorders exclude those induced by a general medical condition. If psychotic symptoms develop shortly after, and apparently in response to, one or more severely stressful events, the disturbance is diagnosed as Brief Psychotic Disorder with Marked Stressor(s) (formerly labeled "brief reactive psychosis" in DSM-III-R). Brief Psychotic Disorder with Marked Stressor(s) is treatable by the glucocorticoid receptor antagonists of the present invention.

Brief Psychotic Disorder with Marked Stressor(s) is generally diagnosed in unstructured clinical interactions, in which skilled clinicians assess whether a patient's symptoms fall within the DSM-IV-TR criteria for the disorder. Brief Psychotic Disorder with Marked Stressor(s) may also be diagnosed with a standardized test instrument in a structured clinical interview. A suitable standardized instrument is First et al., *Structured Clinical Interview for DSM-IV Axis I Disorders, Research Version, Patient Edition With Psychotic Screen (SCID-I/P W/PSY SCREEN)*, New York: Biometrics Research, New York State Psychiatric Institute (1997).

4. General Laboratory Procedures

When practicing the methods of the invention, a number of general laboratory tests can be used to assist in the diagnosis, progress and prognosis of the patient with stress disorders, including monitoring of parameters such as blood cortisol, drug metabolism, brain structure and function and the like. These procedures can be helpful because all patients metabolize and react to drugs uniquely. In addition, such monitoring may be important because each GR antagonist has different pharmacokinetics. Different patients and disease conditions may require different dosage regimens and formulations. Such procedures and means to determine dosage regimens and formulations are well described in the scientific and patent literature. A few illustrative examples are set forth below.

a. Determining Blood Cortisol Levels

Varying levels of blood cortisol, especially high levels of cortisol, have been associated with stress disorders, although the invention may also be practiced upon patients with apparently normal levels of blood cortisol. See Mazure et al., *Biol Psychiatry* 41:865–70 (1997). Thus, monitoring blood cortisol and determining baseline cortisol levels are useful laboratory tests to aid in the diagnosis, treatment and prognosis of a stress disorder patient. A wide variety of laboratory tests exist that can be used to determine whether an individual is normal, hypo- or hypercortisolemic. Stress disorder patients typically have normal levels of cortisol that are often less than 25 $\mu$g/dl in the afternoon, and frequently about 15 $\mu$g/dl or less in the afternoon, although the values often fall at the high end of the normal range, which is generally considered to be 5–15 $\mu$g/dl in the afternoon.

Immunoassays such as radioimmunoassays are commonly used because they are accurate, easy to do and relatively cheap. Because levels of circulating cortisol is an indicator of adrenocortical function, a variety of stimulation and suppression tests, such as ACTH Stimulation, ACTH Reserve, dexamethasone suppression test (see, e.g., Greenwald, *Am. J. Psychiatry* 143:442–446, 1986), can also provide diagnostic, prognostic or other information to be used adjunctively in the methods of the invention.

One such assay available in kit form is the radioimmunoassay available as "Double Antibody Cortisol Kit" (Diagnostic Products Corporation, Los Angeles, Calif.), *Acta Psychiatr. Scand.* 70:239–247, 1984). This test is a competitive radioimmunoassay in which $^{125}$I-labeled cortisol competes with cortisol from an clinical sample for antibody sites. In this test, due to the specificity of the antibody and lack of any significant protein effect, serum and plasma samples require neither preextraction nor predilution. This assay is described in further detail in Example 2, below.

b. Determination of Blood/Urine Mifepristone Levels

Because a patient's metabolism, clearance rate, toxicity levels, etc. differs with variations in underlying primary or secondary disease conditions, drug history, age, general medical condition and the like, it may be necessary to measure blood and urine levels of GR antagonist. Means for such monitoring are well described in the scientific and patent literature. As in one embodiment of the invention mifepristone is administered to treat stress disorders, an illustrative example of determining blood and urine mifepristone levels is set forth in the Example below.

c. Other Laboratory Procedures

Because stress disorders can be heterogeneous, a number of additional laboratory tests can be used adjunctively in the methods of the invention to assist in diagnosis, treatment efficacy, prognosis, toxicity and the like. For example, as increased hypercortisolemia has also been associated with stress disorders, diagnosis and treatment assessment can be augmented by monitoring and measuring glucocorticoid-sensitive variables, including but limited to fasting blood sugar, blood sugar after oral glucose administration, plasma concentrations thyroid stimulating hormone (TSH), corticosteroid-binding globulin, luteinizing hormone (LH), testosterone-estradiol-binding globulin, and/or total and free testosterone.

Laboratory tests monitoring and measuring GR antagonist metabolite generation, plasma concentrations and clearance rates, including urine concentration of antagonist and metabolites, may also be useful in practicing the methods of the invention. For example, mifepristone has two hydrophilic, N-monomethylated and N-dimethylated, metabolites. Plasma and urine concentrations of these metabolites (in addition to Mifepristone) can be determined using, for example, thin layer chromatography, as described in Kawai *Pharmacol. and Experimental Therapeutics* 241:401–406, 1987.

5. Glucocorticoid Receptor Antagonists to Treat Stress Disorders

The invention provides for methods of treating stress disorders utilizing any composition or compound that can block a biological response associated with the binding of cortisol or a cortisol analogue to a GR. Antagonists of GR activity utilized in the methods of the invention are well described in the scientific and patent literature. A few illustrative examples are set forth below.

a. Steroidal Anti-Glucocorticoids as GR Antagonists.

Steroidal glucocorticoid antagonists are administered for the treatment of stress disorders in various embodiments of the invention. Steroidal anti-glucocorticoids can be obtained by modification of the basic structure of glucocorticoid agonists, i.e., varied forms of the steroid backbone. The structure of cortisol can be modified in a variety of ways. The two most commonly known classes of structural modifications of the cortisol steroid backbone to create glucocorticoid antagonists include modifications of the 11-beta hydroxy group and modification of the 17-beta side chain (see, e.g., Lefebvre, *J. Steroid Biochem.* 33:557–563, 1989).

i.) Removal or Substitution of the 11-beta Hydroxy Group

Glucocorticoid agonists with modified steroidal backbones comprising removal or substitution of the 11-beta hydroxy group are administered in one embodiment of the invention. This class includes natural anti-glucocorticoids, including cortexolone, progesterone and testosterone derivatives, and synthetic compositions, such as mifepristone (Lefebvre, et al. supra). Preferred embodiments of the invention include all 11-beta-aryl steroid backbone derivatives because these compounds are devoid of progesterone receptor (PR) binding activity (Agarwal, *FEBS* 217:221–226, 1987). Another preferred embodiment comprises an 11-beta phenyl-aminodimethyl steroid backbone derivative, i.e., mifepristone, which is both an effective anti-glucocorticoid and anti-progesterone agent. These compositions act as reversibly-binding steroid receptor antagonists. For example, when bound to a 11-beta phenyl-aminodimethyl steroid, the steroid receptor is maintained in a conformation that cannot bind its natural ligand, such as cortisol in the case of GR (Cadepond, 1997, supra).

Synthetic 11-beta phenyl-aminodimethyl steroids include mifepristone, also known as RU486, or 17-beta-hydrox-11-beta-(4-dimethyl-aminophenyl) 17-alpha-(1-propynyl)estra-4,9-dien-3-one). Mifepristone has been shown to be a powerful antagonist of both the progesterone and glucocorticoid (GR) receptors. Another 11-beta phenyl-aminodimethyl steroids shown to have GR antagonist effects includes RU009 (RU39.009), 11-beta-(4-dimethyl-aminoethoxyphenyl)-17-alpha-(propynyl-17 beta-hydroxy-4,9-estradien-3-one) (see Bocquel, *J. Steroid Biochem. Molec. Biol.* 45:205–215, 1993). Another GR antagonist related to RU486 is RU044 (RU43.044) 17-beta-hydrox-17-alpha-19-(4-methyl-phenyl)-androsta-4,9(11)-dien-3-one) (Bocquel, 1993, supra). See also Teutsch, *Steroids* 38:651–665, 1981; U.S. Pat. Nos. 4,386,085 and 4,912,097.

One embodiment includes compositions containing the basic glucocorticoid steroid structure which are irreversible anti-glucocorticoids. Such compounds include alpha-keto-methanesulfonate derivatives of cortisol, including cortisol-21-mesylate (4-pregnene-11-beta, 17-alpha, 21-triol-3, 20-dione-21-methane-sulfonate and dexamethasone-21-mesylate (16-methyl-9 alpha-fluoro-1,4-pregnadiene-11 beta, 17-alpha, 21-triol-3, 20-dione-21-methane-sulfonate). See Simons, *J. Steroid Biochem.* 24:2532 1986; Mercier, *J. Steroid Biochem.* 25:11–20, 1986; U.S. Pat. No. 4,296,206.

ii). Modification of the 17-beta Side Chain Group

Steroidal anti-glucocorticoids which can be obtained by various structural modifications of the 17-beta side chain are also used in the methods of the invention. This class includes synthetic anti-glucocorticoids such as dexamethasone-oxetanone, various 17, 21-acetonide derivatives and 17-beta-carboxamide derivatives of dexamethasone (Lefebvre, 1989, supra; Rousseau, *Nature* 279:158–160, 1979).

iii). Other Steroid Backbone Modifications

GR antagonists used in the various embodiments of the invention include any steroid backbone modification which effects a biological response resulting from a GR-agonist interaction. Steroid backbone antagonists can be any natural or synthetic variation of cortisol, such as adrenal steroids missing the C-19 methyl group, such as 19-nordeoxycorticosterone and 19-norprogesterone (Wynne, *Endocrinology* 107:1278–1280, 1980).

In general, the 11-beta side chain substituent, and particularly the size of that substituent, can play a key role in determining the extent of a steroid's anti-glucocorticoid activity. Substitutions in the A ring of the steroid backbone can also be important. 17-hydroxypropenyl side chains generally decrease anti-glucocorticoid activity in comparison to 17-propinyl side chain containing compounds.

Additional glucocorticoid receptor antagonists known in the art and suitable for practice of the invention include 21-hydroxy-6,19-oxidoprogesterone (see Vicent, *Mol. Pharm.* 52:749–753 (1997)), Org31710 (see Mizutani, *J Steroid Biochem Mol Biol* 42(7):695–704 (1992)), Org34517, RU43044, RU40555 (see Kim, *J Steroid Biochem Mol Biol.* 67(3):213–22 (1998)), RU28362, and ZK98299.

b. Non-Steroidal Anti-Glucocorticoids as Antagonists.

Non-steroidal glucocorticoid antagonists are also used in the methods of the invention to treat stress disorders. These include synthetic mimetics and analogs of proteins, including partially peptidic, pseudopeptidic and non-peptidic molecular entities. For example, oligomeric peptidomimetics useful in the invention include (alpha-betaunsaturated) peptidosulfonamides, N-substituted glycine derivatives, oligo carbamates, oligo urea peptidomimetics, hydrazinopeptides, oligosulfones and the like (see, e.g., Amour, *Int. J. Pept. Protein Res.* 43:297–304, 1994; de Bont, *Bioorganic & Medicinal Chem.* 4:667–672, 1996). The creation and simultaneous screening of large libraries of synthetic molecules can be carried out using well-known techniques in combinatorial chemistry, for example, see van Breemen, *Anal Chem* 69:2159–2164, 1997; and Lam, *Anticancer Drug Des* 12:145–167, 1997. Design of peptidomimetics specific for GR can be designed using computer programs in conjunction with combinatorial chemistry (combinatorial library) screening approaches (Murray, *J. of Computer-Aided Molec. Design* 9:381–395, 1995; Bohm, *J. of Computer-Aided Molec. Design* 10:265–272, 1996). Such "rational drug design" can help develop peptide isomerics and conformers including cycloisomers, retro-inverso isomers, retro isomers and the like (as discussed in Chorev, *TibTech* 13:438–445, 1995).

c. Identifying Specific Glucocorticoid Receptor Antagonists

Because any specific GR antagonist can be used for the treatment of stress disorders in the methods of the invention, in addition to the compounds and compositions described above, additional useful GR antagonists can be determined by the skilled artisan. A variety of such routine, well-known methods can be used and are described in the scientific and patent literature. They include in vitro and in vivo assays for the identification of additional GR antagonists. A few illustrative examples are described below.

One assay that can be used to identify a GR antagonist of the invention measures the effect of a putative GR antagonist on tyrosine amino-transferase activity in accordance with the method of Granner, *Meth. Enzymol.* 15:633, 1970. This analysis is based on measurement of the activity of the liver enzyme tyrosine amino-transferase (TAT) in cultures of rat hepatoma cells (RHC). TAT catalyzes the first step in the metabolism of tyrosine and is induced by glucocorticoids (cortisol) both in liver and hepatoma cells. This activity is easily measured in cell extracts. TAT converts the amino group of tyrosine to 2-oxoglutaric acid. P-hydroxyphenylpyruvate is also formed. It can be converted to the more stable p-hydroxybenzaldehyde in an alkaline solution and quantitated by absorbance at 331 nm. The putative GR antagonist is co-administered with cortisol to whole liver, in vivo or ex vivo, or hepatoma cells or cell extracts. A compound is identified as a GR antagonist when its administration decreases the amount of induced TAT activity, as compared to control (i.e., only cortisol or GR agonist added) (see also Shirwany, *Biochem. Biophys. Acta* 886:162–168, 1986).

Further illustrative of the many assays which can be used to identify compositions utilized in the methods of the invention, in addition to the TAT assay, are assays based on glucocorticoid activities in vivo. For example, assays that assess the ability of a putative GR antagonist to inhibit uptake of $^3$H-thymidine into DNA in cells which are stimulated by glucocorticoids can be used. Alternatively, the putative GR antagonist can complete with $^3$H-dexamethasone for binding to a hepatoma tissue culture GR (see, e.g., Choi, et al., *Steroids* 57:313–318, 1992). As another example, the ability of a putative GR antagonist to block nuclear binding of $^3$H-dexamethasone-GR complex can be used (Alexandrova et al., *J. Steroid Biochem. MoL Biol.* 41:723–725, 1992). To further identify putative GR antagonists, kinetic assays able to discriminate between glucocorticoid agonists and antagonists by means of receptor-binding kinetics can also be used (as described in Jones, *Biochem J.* 204:721–729, 1982).

In another illustrative example, the assay described by Daune, *Molec. Pharm.* 13:948–955, 1977; and in U.S. Pat. No. 4,386,085, can be used to identify anti-glucocorticoid activity. Briefly, the thymocytes of adrenalectomized rats are incubated in nutritive medium containing dexamethasone with the test compound (the putative GR antagonist) at varying concentrations. $^3$H-uridine is added to the cell culture, which is further incubated, and the extent of incorporation of radiolabel into polynucleotide is measured. Glucocorticoid agonists decrease the amount of $^3$H-uridine incorporated. Thus, a GR antagonist will oppose this effect.

For additional compounds that can be utilized in the methods of the invention and methods of identifying and making such compounds, see U.S. Pat. Nos.: U.S. Pat. No. 4,296,206 (see above); U.S. Pat. No. 4,386,085 (see above); U.S. Pat. Nos. 4,447,424; 4,477,445; 4,519,946; 4,540,686; 4,547,493; 4,634,695; 4,634,696; 4,753,932; 4,774,236; 4,808,710; 4,814,327; 4,829,060; 4,861,763; 4,912,097; 4,921,638; 4,943,566; 4,954,490; 4,978,657; 5,006,518; 5,043,332; 5,064,822; 5,073,548; 5,089,488; 5,089,635; 5,093,507; 5,095,010; 5,095,129; 5,132,299; 5,166,146; 5,166,199; 5,173,405; 5,276,023; 5,380,839; 5,348,729; 5,426,102; 5,439,913; and 5,616,458; and WO 96/19458, which describes non-steroidal compounds which are high-affinity, highly selective modulators (antagonists) for steroid receptors, such as 6-substituted-1,2-dihydro N-1 protected quinolines.

The specificity of the antagonist for the GR relative to the MR can be measured using a variety of assays known to those of skill in the art. For example, specific antagonists can be identified by measuring the ability of the antagonist to bind to the GR compared to the MR (see, e.g., U.S. Pat. Nos. 5,606,021; 5,696,127; 5,215,916; 5,071,773). Such an analysis can be performed using either direct binding assay or by assessing competitive binding to the purified GR or MR in the presence of a known antagonist. In an exemplary assay, cells that are stably expressing the glucocorticoid receptor or mineralocorticoid receptor (see, e.g., U.S. Pat. No. 5,606,021) at high levels are used as a source of purified receptor. The affinity of the antagonist for the receptor is then directly measured. Those antagonists that exhibit at least a 100-fold higher affinity, often 1000-fold, for the GR relative to the MR are then selected for use in the methods of the invention.

A GR-specific antagonist may also be defined as a compound that has the ability to inhibit GR-mediated activities, but not MR-mediated activities. One method of identifying such a GR-specific antagonist is to assess the ability of an antagonist to prevent activation of reporter constructs using transfection assays (see, e.g., Bocquel et al, *J. Steroid Biochem Molec. Biol* 45:205–215, 1993, U.S. Pat. Nos. 5,606,021, 5,929,058). In an exemplary transfection assay, an expression plasmid encoding the receptor and a reporter plasmid containing a reporter gene linked to receptor-specific regulatory elements are cotransfected into suitable receptor-negative host cells. The transfected host cells are then cultured in the presence and absence of a hormone, such as cortisol or analog thereof, able to activate the hormone responsive promoter/enhancer element of the reporter plasmid. Next the transfected and cultured host cells are monitored for induction (i.e., the presence) of the product of the reporter gene sequence. Finally, the expression and/or steroid binding-capacity of the hormone receptor protein (coded for by the receptor DNA sequence on the expression plasmid and produced in the transfected and cultured host cells), is measured by determining the activity of the reporter gene in the presence and absence of an antagonist. The antagonist activity of a compound may be determined in comparison to known antagonists of the GR and MR receptors (see, e.g., U.S. Pat. No. 5,696,127). Efficacy is then reported as the percent maximal response observed for each compound relative to a reference antagonist compound. A GR-specific antagonist is considered to exhibit at least a 100-fold, often 1000-fold or greater, activity towards the GR relative to the MR.

6. Treatment of Stress Disorders Using Glucocorticoid Receptor Antagonists

Anti-glucocorticoids, such as mifepristone, are formulated as pharmaceuticals to be used in the methods of the invention to treat stress disorders. Any composition or compound that can block a biological response associated with the binding of cortisol or a cortisol analogue to a GR can be used as a pharmaceutical in the invention. Routine means to determine GR antagonist drug regimens and formulations to practice the methods of the invention are well described in the patent and scientific literature, and some illustrative examples are set forth below.

a. Glucocorticoid Receptor Antagonists as Pharmaceutical Compositions

The GR antagonists used in the methods of the invention can be administered by any means known in the art, e.g., parenterally, topically, orally, or by local administration, such as by aerosol or transdermally. The methods of the invention provide for prophylactic and/or therapeutic treatments. The GR antagonists as pharmaceutical formulations can be administered in a variety of unit dosage forms depending upon the condition or disease and the degree of dementia, the general medical condition of each patient, the resulting preferred method of administration and the like. Details on techniques for formulation and administration are well described in the scientific and patent literature, see, e.g., the latest edition of Remington's Pharmaceutical Sciences, Maack Publishing Co, Easton Pa. ("Remington's").

GR antagonist pharmaceutical formulations can be prepared according to any method known to the art for the manufacture of pharmaceuticals. Such drugs can contain sweetening agents, flavoring agents, coloring agents and preserving agents. Any GR antagonist formulation can be admixtured with nontoxic pharmaceutically acceptable excipients which are suitable for manufacture.

Pharmaceutical formulations for oral administration can be formulated using pharmaceutically acceptable carriers well known in the art in appropriate and suitable dosages. Such carriers enable the pharmaceutical formulations to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be obtained through combination of GR antagonist compounds with a solid excipient, optionally grinding a resulting mixture, and processing the mixture of granules, after adding suitable additional compounds, if desired, to obtain tablets or dragee cores. Suitable solid excipients are carbohydrate or protein fillers include, but are not limited to, sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain GR antagonist mixed with a filler or binders such as lactose or starches, lubricants such as talc or magnesium stearate, and, optionally, stabilizers. In soft capsules, the GR antagonist compounds may be dissolved or suspended in suitable liquids, such as fatty oils, liquid paraffin, or liquid polyethylene glycol with or without stabilizers.

Aqueous suspensions of the invention contain a GR antagonist in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil suspensions can be formulated by suspending a GR antagonist in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol Exp. Ther.* 281:93–102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

Dispersible powders and granules of the invention suitable for preparation of an aqueous suspension by the addition of water can be formulated from a GR antagonist in admixture with a dispersing, suspending and/or wetting agent, and one or more preservatives. Suitable dispersing or wetting agents and suspending agents are exemplified by those disclosed above. Additional excipients, for example, sweetening, flavoring and coloring agents, can also be present.

The GR antagonists of this invention can also be administered in the form of suppositories for rectal administration of the drug. These formulations can be prepared by mixing the drug with a suitable non-irritating excipient which is solid at ordinary temperatures but liquid at the rectal temperatures and will therefore melt in the rectum to release the drug. Such materials are cocoa butter and polyethylene glycols.

The GR antagonists of this invention can also be administered by in intranasal, intraocular, intravaginal, and intrarectal routes including suppositories, insufflation, powders and aerosol formulations (for examples of steroid inhalants, see Rohatagi, *J. Clin. Pharmacol.* 35:1187–1193, 1995; Tjwa, *Ann. Allergy Asthma Immunol.* 75:107–111, 1995).

The GR antagonists of the invention can be delivered by transdermally, by a topical route, formulated as applicator sticks, solutions, suspensions, emulsions, gels, creams, ointments, pastes, jellies, paints, powders, and aerosols.

The GR antagonists of the invention can also be delivered as microspheres for slow release in the body. For example, microspheres can be administered via intradermal injection of drug (e.g., mifepristone)-containing microspheres, which slowly release subcutaneously (see Rao, *J. Biomater Sci. Polym. Ed.* 7:623–645, 1995; as biodegradable and injectable gel formulations (see, e.g., Gao *Pharm. Res.* 12:857–863, 1995); or, as microspheres for oral administration (see, e.g., Eyles, *J. Pharm. Pharmacol.* 49:669–674, 1997). Both transdermal and intradermal routes afford constant delivery for weeks or months.

The GR antagonist pharmaceutical formulations of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5, that is combined with buffer prior to use In another embodiment, the GR antagonist formulations of the invention are useful for parenteral administration, such as intravenous (IV) administration or administration into a body cavity or lumen of an organ. The formulations for administration will commonly comprise a solution of the GR antagonist (e.g., mifepristone) dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of GR antagonist in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the GR antagonist formulations of the invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the GR antagonist into the target cells in vivo. (See, e.g., Al-Muhammed, *J. Microencapsul.* 13:293–306, 1996; Chonn, *Curr. Opin. Biotechnol.* 6:698–708, 1995; Ostro, *Am. J. Hosp. Pharm.* 46:1576–1587, 1989).

b. Determining Dosing Regimens for Glucocorticoid Receptor Antagonists

The methods of the invention treat stress disorders, i.e., reduce the incidence and severity of dissociative and re-experiencing symptoms. The amount of GR antagonist adequate to accomplish this is defined as a "therapeutically effective dose". The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the GR antagonists' rate of absorption, bioavailability, metabolism, clearance, and the like (see, e.g., Hidalgo-Aragones (1996) *J. Steroid Biochem. Mol. Biol.* 58:611–617; Groning (1996) *Pharmazie* 51:337–341; Fotherby (1996) *Contraception* 54:59–69; Johnson (1995) *J. Pharm. Sci.* 84:1144–1146; Rohatagi (1995) *Pharmazie* 50:610–613; Brophy (1983) *Eur. J. Clin. Pharmacol.* 24:103–108; the latest Remington's, supra). For example, in one study, less than 0.5% of the daily dose of mifepristone was excreted in the urine; the drug bound extensively to circulating albumin (see Kawai (1989) supra). The state of the art allows the clinician to determine the dosage regimen for each individual patient, GR antagonist and disease or condition treated. As an illustrative example, the guidelines provided below for mifepristone can be used as guidance to determine the dosage regiment, i.e., dose schedule and dosage levels, of any GR antagonist administered when practicing the methods of the invention.

Single or multiple administrations of GR antagonist formulations can be administered depending on the dosage and frequency as required and tolerated by the patient. The formulations should provide a sufficient quantity of active agent, i.e., mifepristone, to effectively treat the dementia. Thus, one typical pharmaceutical formulations for oral administration of mifepristone is in a daily amount of between about 0.5 to about 20 mg per kilogram of body weight per day. In an alternative embodiment, dosages are from about 1 mg to about 4 mg per kg of body weight per patient per day are used. Lower dosages can be used, particularly when the drug is administered to an anatomically secluded site, such as the cerebral spinal fluid (CSF) space, in contrast to administration orally, into the blood stream, into a body cavity or into a lumen of an organ. Substantially higher dosages can be used in topical administration. Actual methods for preparing parenterally administrable GR antagonist formulations will be known or apparent to those skilled in the art and are described in more detail in such publications as Remington's, supra. See also Nieman, In "Receptor Mediated Antisteroid Action," Agarwal, et al., eds., De Gruyter, N.Y. (1987).

After a pharmaceutical comprising a GR antagonist of the invention has been formulated in a acceptable carrier, it can be placed in an appropriate container and labeled for treatment of an indicated condition. For administration of GR antagonists, such labeling would include, e.g., instructions concerning the amount, frequency and method of administration. In one embodiment, the invention provides for a kit for the treatment of dementia in a human which includes a GR antagonist and instructional material teaching the indications, dosage and schedule of administration of the GR antagonist.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

The following examples are offered to illustrate, but not to limit the claimed invention.

Example 1

Treating Stress Disorders with Mifepristone

The following example demonstrates how to practice the methods of the invention.

Patient Selection

Individuals are diagnosed with Acute Stress Disorder, Post-Traumatic Stress Disorder, or Brief Psychotic Disorder with Marked Stressor(s) using subjective and objective criteria, including criteria as set forth by the DSM-IV-TR, as described above. The stress disorder patient typically has normal, increased, or decreased levels of cortisol for his or her age, although patients recently exposed to an acute stressor may have especially increased cortisol levels.

Dosage Regimen and Administration of Mifepristone

The glucocorticoid receptor (GR) antagonist, mifepristone, is used in this study. It is administered in dosages of 200 mg daily. Individuals will be given 200 mg of mifepristone daily for six months and evaluated as described below. Dosages will be adjusted if necessary and further evaluations will be performed periodically throughout treatment.

Mifepristone tablets are available from Shanghai HuaLian Pharmaceuticals Co., Ltd., Shanghai, China.

Assessing Treatment of Stress Disorders

To delineate and assess the effectiveness of mifepristone in ameliorating the symptoms of stress disorders, formal psychiatric assessment and a battery of neuro-psychological tests and assessments are administered to all patients. The patients' performance on a standardized test instrument appropriate to the stress disorder under study will be determined. These tests and diagnostic assessments take place at baseline (patient's entry into treatment) and periodically throughout treatment.

Example 2

Measuring Cortisol Levels

To measure cortisol levels of the patients of Example 1, afternoon Cortisol Test measurements are taken and used as the baseline cortisol measure. Cortisol levels are taken at Day 0, at two weeks after receiving the medication (Day 14), and each visit for up to six months and periodically thereafter.

The "Double Antibody Cortisol Kit" (Diagnostic Products Corporation, Los Angeles, Calif.) is used to measure blood cortisol levels. This test is a competitive radioimmunoassay in which $^{125}$I-labeled cortisol competes with cortisol from an clinical sample for antibody sites, and is performed essentially according to manufacturer's instructions using reagents supplied by manufacturer. Briefly, blood is collected by venipuncture and serum separated from the cells. The samples are stored at 2 to 8° C. for up to seven days, or up to two month frozen at −20° C. Before the assay, samples are allowed to come up to room temperature (15–28° C.) by gentle swirling or inversion. Sixteen tubes in duplicate at 25 microliters of serum per tube are prepared. Cortisol concentrations is calculated from the prepared calibration tubes. Net counts equals the average CPM minus the average non-specific CPM. Cortisol concentrations for the unknowns is estimated by interpolation from the calibration curve (Dudley, et al. (1985) Clin. Chem. 31:1264–1271).

It is understood that the examples and embodiments described herein are for illustrative purposes only and that various modifications or changes in light thereof will be suggested to persons skilled in the art and are to be included within the spirit and purview of this application and scope of the claims.

What is claimed is:

1. A method of ameliorating the symptoms of a stress disorder in a patient in need thereof by administration of an amount of a glucocorticoid receptor antagonist effective to ameliorate the symptoms of the stress disorder, wherein the stress disorder is selected from the group consisting of Acute Stress Disorder and Brief Psychotic Disorder With Marked Stressor(s), with the proviso that the patient be not otherwise in need of treatment with a glucocorticoid receptor antagonist.

2. The method of claim 1, wherein the glucocorticoid receptor antagonist comprises a steroidal skeleton with at least one phenyl-containing moiety in the 11-beta position of the steroidal skeleton.

3. The method of claim 2, wherein the phenyl-containing moiety in the 11-beta position of the steroidal skeleton is a dimethylaminophenyl moiety.

4. The method of claim 3, wherein the glucocorticoid receptor antagonist comprises mifepristone.

5. The method of claim 4, wherein the glucocorticoid receptor antagonist is selected from the group consisting of RU009 and RU044.

6. The method of claim 1, wherein the glucocorticoid receptor antagonist is administered in a daily amount of between about 0.5 to about 20 mg per kilogram of body weight per day.

7. The method of claim 6, wherein the glucocorticoid receptor antagonist is administered in a daily amount of between about 1 to about 10 mg per kilogram of body weight per day.

8. The method of claim 7, wherein the glucocorticoid receptor antagonist is administered in a daily amount of between about 1 to about 4 mg per kilogram of body weight per day.

9. The method of claim 1, wherein the administration is once per day.

10. The method of claim 1, wherein the mode of administration is oral.

11. The method of claim 1, wherein the mode of administration is by a transdermal application, by a nebulized suspension, or by an aerosol spray.

12. A method of ameliorating the emergence of stress disorder symptoms in a patient exposed to a traumatic stressor, the method comprising administering an effective amount of a glucocorticoid receptor antagonist to the patient within 30 days of exposure to the traumatic stressor.

13. The method of claim 1 wherein the stress disorder is Acute Stress Disorder.

14. The method of claim 1 wherein the stress disorder is Brief Psychotic Disorder With Marked Stressor(s).

15. A method of reducing the symptoms of a stress disorder in a patient in need thereof by administration of an amount of a glucocorticoid receptor antagonist effective to ameliorate the symptoms of the stress disorder, wherein the stress disorder is selected from the group consisting of Acute Stress Disorder and Brief Psychotic Disorder With Marked Stressor(s), with the proviso that the patient be not otherwise in need of treatment with a glucocorticoid receptor antagonist.

16. The method of claim 15 wherein administration is given within 30 days of exposure to a traumatic stressor.

* * * * *